(12) United States Patent
Kamei et al.

(10) Patent No.: US 11,867,693 B2
(45) Date of Patent: Jan. 9, 2024

(54) SEMI-QUANTITATIVE LATERAL-FLOW IMMUNOASSAY FOR THE DETECTION OF CSF LEAKS

(71) Applicant: The Regents of the University of California, Oakland, CA (US)

(72) Inventors: Daniel Takashi Kamei, Monterey Park, CA (US); Maie A. St. John, Los Angeles, CA (US); Zachary D. Taylor, Los Angeles, CA (US); Daniel William Bradbury, Los Angeles, CA (US); Ashley Elizabeth Kita, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 89 days.

(21) Appl. No.: 17/530,336

(22) Filed: Nov. 18, 2021

(65) Prior Publication Data

US 2022/0146507 A1 May 12, 2022

Related U.S. Application Data

(63) Continuation of application No. 16/498,312, filed as application No. PCT/US2018/024392 on Mar. 26, 2018, now Pat. No. 11,209,427.
(Continued)

(51) Int. Cl.
*G01N 33/543* (2006.01)
*B01L 3/00* (2006.01)

(52) U.S. Cl.
CPC ...... *G01N 33/54386* (2013.01); *B01L 3/5023* (2013.01); *B01L 2400/0406* (2013.01); *G01N 2333/99* (2013.01)

(58) Field of Classification Search
None
See application file for complete search history.

(56) References Cited

U.S. PATENT DOCUMENTS

| 5,141,850 A | 8/1992 | Cole et al. |
| 6,194,221 B1 | 2/2001 | Rehg et al. |
| (Continued) | | |

FOREIGN PATENT DOCUMENTS

| CN | 106662582 A | 5/2017 |
| EP | 1064553 A1 | 1/2001 |
| (Continued) | | |

OTHER PUBLICATIONS

Bernasconi et al., Retrospective validation of a β-trace protein interpretation algorithm for the diagnosis of cerebrospinal fluid leakage, published online Sep. 22, 2016, Clin Chem Med, 55(4), pp. 554-560 (Year: 2016).*

(Continued)

*Primary Examiner* — Holly Kipouros
(74) *Attorney, Agent, or Firm* — Tom Hunter; Weaver Austin Villeneuve & Sampson LLP (57) ABSTRACT

Devices and methods are provided for the detection of CSF in a biological sample. In certain embodiments the device is a lateral flow device comprising: a porous substrate; a sample addition zone disposed on or in said porous substrate; a detection zone disposed on or in said porous substrate where said detection zone comprises at least a first test line (T1) and a second test line (T2) each test line comprising binding moieties that bind a complex formed between beta-trace protein (βTP) and an indicator attached to a βTP binding molecule; wherein said porous substrate defines a flow path through which a sample applied to the sample addition zone flows under capillary action away from said sample addition zone into said detection zone; and wherein said first test line (T1) and said second test line (T2)

(Continued)

are is configured so that either no test line signal or just a signal at the first test line (T1) is detectable when βTP concentration in a sample applied to said device is lower than the βTP level indicative of a CSF leak; and said second test line (T2) is configured so that a signal is detectable at said second test line when βTP concentration in a sample applied to said device is greater than the βTP level indicative of a CSF leak.

19 Claims, 4 Drawing Sheets

Related U.S. Application Data (60) Provisional application No. 62/477,230, filed on Mar. 27, 2017.

(56) References Cited

U.S. PATENT DOCUMENTS

| | | |
|---|---|---|
| 6,855,561 B2 | 2/2005 | Jerome et al. |
| 6,924,153 B1 | 8/2005 | Boehringer et al. |
| 6,979,576 B1 | 12/2005 | Cheng et al. |
| 7,179,657 B2 | 2/2007 | Jerome et al. |
| 7,226,793 B2 | 6/2007 | Jerome et al. |
| 7,459,314 B2 | 12/2008 | Guo et al. |
| 7,537,937 B2 | 5/2009 | Jerome et al. |
| 7,553,675 B2 | 6/2009 | Jerome et al. |
| 7,666,614 B2 | 2/2010 | Cheng et al. |
| 7,794,656 B2 | 9/2010 | Liang et al. |
| 7,867,780 B2 | 1/2011 | Jones et al. |
| 7,932,099 B2 | 4/2011 | Egan et al. |
| 8,003,765 B2 | 8/2011 | Pentyala |
| 8,030,091 B2 | 10/2011 | Jerome et al. |
| 8,193,002 B2 | 6/2012 | Guo et al. |
| 8,377,710 B2 | 2/2013 | Whitesides et al. |
| 8,445,293 B2 | 5/2013 | Babu et al. |
| 8,603,832 B2 | 12/2013 | Whitesides et al. |
| 8,628,729 B2 | 1/2014 | Carrilho et al. |
| 8,828,739 B2 | 9/2014 | Guo et al. |
| 9,193,988 B2 | 11/2015 | Whitesides et al. |
| 9,207,236 B2 | 12/2015 | Cary |
| 9,250,236 B2 | 2/2016 | Babu et al. |
| 9,347,955 B2 | 5/2016 | Pieribone |
| 9,823,247 B2 | 11/2017 | Kamei et al. |
| 10,006,911 B2 | 6/2018 | Kamei et al. |
| 10,359,423 B2 | 7/2019 | Kamei et al. |
| 10,578,616 B2 | 3/2020 | Kamei et al. |
| 11,209,427 B2 | 12/2021 | Kamei et al. |
| 11,287,426 B2 | 3/2022 | Kamei et al. |
| 11,327,075 B2 | 5/2022 | Kamei et al. |
| 11,635,432 B2 | 4/2023 | Kamei et al. |
| 2003/0215358 A1 | 11/2003 | Schulman et al. |
| 2004/0002168 A1 | 1/2004 | Remington et al. |
| 2004/0203079 A1 | 10/2004 | Pentyala |
| 2004/0214171 A1 | 10/2004 | Yamashita et al. |
| 2004/0241752 A1 | 12/2004 | Anderson et al. |
| 2005/0239216 A1 | 10/2005 | Feistel |
| 2006/0019406 A1 | 1/2006 | Wei et al. |
| 2006/0025579 A1 | 2/2006 | Riedl et al. |
| 2007/0003992 A1 | 1/2007 | Pentyala |
| 2007/0140911 A1 | 6/2007 | Carney et al. |
| 2007/0196864 A1 | 8/2007 | Pentyala |
| 2007/0292902 A1 | 12/2007 | Cheng et al. |
| 2008/0081341 A1 | 4/2008 | Maher et al. |
| 2008/0138842 A1 | 6/2008 | Boehringer et al. |
| 2008/0227113 A1 | 9/2008 | Pentyala |
| 2008/0227220 A1 | 9/2008 | Franse et al. |
| 2008/0254440 A1 | 10/2008 | Uchida et al. |
| 2009/0110601 A1 | 4/2009 | Levi et al. |
| 2009/0191648 A1 | 7/2009 | Bohannon |
| 2010/0227323 A1 | 9/2010 | Baeumner et al. |
| 2011/0003310 A1 | 1/2011 | Ennis et al. |
| 2011/0072885 A1 | 3/2011 | Inana et al. |
| 2011/0151479 A1 | 6/2011 | Stevens et al. |
| 2011/0312074 A1 | 12/2011 | Azimi et al. |
| 2012/0107956 A1 | 5/2012 | Boehringer et al. |
| 2012/0238008 A1 | 9/2012 | Henry et al. |
| 2013/0065784 A1 | 3/2013 | Takayama et al. |
| 2013/0102063 A1 | 4/2013 | Levi et al. |
| 2013/0266956 A1 | 10/2013 | Tia et al. |
| 2014/0004539 A1 | 1/2014 | Simon et al. |
| 2014/0038222 A1 | 2/2014 | Alt et al. |
| 2014/0228549 A1 | 8/2014 | Schembecker et al. |
| 2015/0017656 A1 | 1/2015 | Wang |
| 2015/0099656 A1 | 4/2015 | Manuguerra et al. |
| 2015/0198592 A1 | 7/2015 | Wang |
| 2015/0253320 A1 | 9/2015 | Kamei et al. |
| 2015/0323534 A1 | 11/2015 | Egan et al. |
| 2016/0266119 A1 | 9/2016 | Sambursky et al. |
| 2016/0282343 A1 | 9/2016 | Jeyendran et al. |
| 2016/0313307 A1 | 10/2016 | Titmus et al. |
| 2016/0334397 A1 | 11/2016 | Yan et al. |
| 2017/0323441 A1 | 11/2017 | Shah et al. |
| 2018/0100854 A1 | 4/2018 | Kamei et al. |
| 2018/0188256 A1 | 7/2018 | Wong |
| 2018/0259521 A1 | 9/2018 | Kamei et al. |
| 2019/0004057 A1* | 1/2019 | Kwon .................... G01N 33/68 |
| 2019/0033308 A1 | 1/2019 | Kamei et al. |
| 2019/0187140 A1 | 6/2019 | Kamei et al. |
| 2019/0250156 A1 | 8/2019 | Kamei et al. |
| 2019/0391143 A1 | 12/2019 | Kamei et al. |
| 2020/0033336 A1 | 1/2020 | Kamei et al. |
| 2020/0124595 A1 | 4/2020 | Irudayaraj et al. |
| 2020/0150116 A1 | 5/2020 | Kamei et al. |
| 2020/0284791 A1 | 9/2020 | Kamei et al. |
| 2022/0252598 A1 | 8/2022 | Kamei et al. |

FOREIGN PATENT DOCUMENTS

| | | |
|---|---|---|
| EP | 1340085 A1 | 9/2003 |
| EP | 1436592 A1 | 7/2004 |
| EP | 1733233 A2 | 12/2006 |
| EP | 1771734 A1 | 4/2007 |
| EP | 0941468 B1 | 7/2007 |
| EP | 2076775 A2 | 7/2009 |
| EP | 2126569 A2 | 12/2009 |
| EP | 2245135 A2 | 11/2010 |
| EP | 2426498 A1 | 3/2012 |
| ES | 2382381 T3 | 6/2012 |
| JP | H03130663 A | 6/1991 |
| JP | 2003250575 A | 9/2003 |
| JP | 2007500363 A | 1/2007 |
| JP | 2008537119 A | 9/2008 |
| JP | 2011075366 A | 4/2011 |
| JP | 2013531259 A | 8/2013 |
| JP | 2013181870 A | 9/2013 |
| KR | 20080103200 A | 11/2008 |
| WO | WO-9818964 A1 | 5/1998 |
| WO | WO-2004081528 A2 | 9/2004 |
| WO | WO-2005042579 A1 | 5/2005 |
| WO | WO-2005074609 A2 | 8/2005 |
| WO | WO-2005098439 A2 | 10/2005 |
| WO | WO-2007092302 A2 | 8/2007 |
| WO | WO-2008043040 A2 | 4/2008 |
| WO | WO-2011116256 A2 | 9/2011 |
| WO | WO-2011159537 A2 | 12/2011 |
| WO | WO-2012010666 A1 | 1/2012 |
| WO | WO-2013105090 A1 | 7/2013 |
| WO | WO-2015134938 A1 | 9/2015 |
| WO | WO-2017041030 A1 | 3/2017 |
| WO | WO-2017214315 A1 | 12/2017 |
| WO | WO-2018039139 A1 | 3/2018 |
| WO | WO-2018183211 A1 | 10/2018 |
| WO | WO-2018222765 A1 | 12/2018 |

OTHER PUBLICATIONS

Leung et al., InfectCheck CRP barcode-style lateral flow assay for semi-quantitative detection of C-reactive protein in distinguishing between bacterial and viral infections, 2008, Journal of Immunological Methods, 336, pp. 30-36 (Year: 2008).*

(56) References Cited

OTHER PUBLICATIONS

Ahmed (2015) "Hydrogel: Preparation, characterization, and applications: A review" J. Adv. Res., 6:105-121.
Arrer et al. (2002) "β-Trace Protein as a Marker for Cerebrospinal Fluid Rhinorrhea" Clin. Chem. 48(6): 939-941.
AU Examination report No. 1 dated May 24, 2021 issued in AU 2020201579.
AU Examination report No. 1 dated Oct. 8, 2019 issued in AU 2015226930.
AU Office Action dated Nov. 4, 2021 issued in AU 2016318103.
Bachmann et al. (2002) "Predictive values of beta-trace protein (prostaglandin D synthase) by use of laser-nephelometry assay for the identification of cerebrospinal fluid." Neurosurgery, 50(3): 571-577.
Carter and Cary (2007) "Lateral flow microarrays: a novel platform for rapid nucleic acid detection based on miniaturized lateral flow chromatography," Nucleic Acids Research 35(10): e74 (11 pages).
Center for Disease Control and Prevention. Diagnostic Tests for Zika Virus. "Updated Guidance for US Laboratories Testing for Zika Virus Infection Jul. 24, 2017"; Availabe at: https://www.cdc.gov/zika/transmission/index.html, 16 pages.
Chiu, et al. (2010) "Generation of Porous Poly(Ethylene Glycol) Hydrogels by Salt Leaching." Tissue Engineering Part C: Methods 16: 905-912.
Chiu et al. (2014) "Biomarker concentration and detection directly on paper," abstract, MicroTAS Annual Meeting, San Antonio, Texas, 3 pages.
Chiu et al. (2014) "Dextran-coated gold nanoprobes for the concentration and detection of protein biomarkers," Annals of Biomedical Engineering 42(11): 2322-2332.
Chiu et al. (2014) "Simultaneous concentration and detection of biomarkers on paper," Lab Chip 14: 3021-3028.
Chiu et al. (2014) "Simultaneous concentration and detection of biomarkers on paper," poster presentation, MicroTAS Annual Meeting, San Antonio, Texas, 1 page.
Chiu et al. (2014) "Simultaneously concentrating and detecting biomarkers on paper," abstract of podium presentation, The Biomedical Engineering Society Annual Meeting, San Antonio, Texas, 1 page.
Chiu et al. (2014) "Simultaneously concentrating and detecting biomarkers on paper," slides from podium presentation, The Biomedical Engineering Society Annual Meeting, San Antonio, Texas, 52 slides.
Chiu et al. (2014) "Manipulating gold nanoparticles to achieve effective and rapid detection of protein biomarkers for resource-poor settings," slides from presentation, not published/distributed. The Annual UC System wide Bioengineering Symposium, Irvine, California, 24 slides.
Chiu et al. (2014) "Polymer-coated gold nanoprobes for the concentration and detection of protein biomarkers for resource-poor settings," The Biomedical Engineering Society Annual Meeting, San Antonio, Texas, poster, 1 page.
Chiu et al. (2014) "Polymer-coated gold nanoprobes for the concentration and detection of protein biomarkers for resource-poor settings," The Biomedical Engineering Society Annual Meeting, San Antonio, Texas, published abstract, 1 page.
Chiu et al., (2015) "An aqueous two-phase system for the concentration and extraction of proteins from the interface for detection using the lateral-flow immunoassay," PLoS One 10: e0142654 (14 pages).
Chiu et al. (2015) "Creating the gold standard point-of-care test for sexually transmitted infections," 20 slide deck, not published, not distributed, for judging only, OneStart Competition, 20 pages.
Chiu et al. (2015) "Creating the gold standard point-of-care test for sexually transmitted infections," 3 minute/3 slide deck, OneStart Competition, 3 pages.
Cho, et al. (2013) "Lateral-flow enzyme immunoconcentration for rapid detection of Listeria monocytogenes." Anal Bioanal Chem 405:3313-3319.

CN First Office Action dated Jan. 22, 2018 issued in CN 201580023439.9.
CN First Office Action dated Mar. 27, 2020 issued in CN 201680059385.6.
CN Second Office Action dated Feb. 20, 2021 issued in CN 201680059385.6.
CN Second Office Action dated Nov. 29, 2018 issued in CN 201580023439.9.
CN Third Office Action dated Jun. 22, 2021 issued in CN 201680059385.6.
EP 2nd Office Action dated Jul. 27, 2021 issued in EP 17810966.6.
EP Extended Search Report dated Mar. 23, 2021 issued in EP 20200335.6.
EP Extended Search Report dated Oct. 26, 2017 issued in EP 15758881.5.
EP Extended Supplementary Search Report dated Dec. 6, 2019 issued in EP 17810966.6.
EP Extended Supplementary Search Report dated Jan. 27, 2021 issued in EP 18809609.3.
EP Extended Supplementary Search Report dated Jun. 14, 2019 issued in EP 16843134.4.
EP Office Action dated Oct. 6, 2020 issued in EP 17810966.6.
EP Partial Supplementary Search Report dated Feb. 4, 2019 issued in EP 16843134.4.
Fang et al. (2011) "Barcode lateral flow immunochromatographic strip for prostate acid phosphatase determination," J. Pharmaceut. Biomed. Anal., 56(5): 1035-1040.
Fu et al. (2011) "Enhanced sensitivity of lateral flow tests using a two-dimensional paper network format," Anal. Chem. 83(20): 7941-7946 (NIH Public Access—Author Manuscript—12 pages).
Fung et al. (2009) "Development of a creatinine enzyme-based bar-code-style lateral-flow assay," Analytical and Bioanalytical Chemistry, 393(4): 1281-1287.
Fung et al. (2009) "Development of enzyme-based bar code-style lateral-flow assay for hydrogen peroxide determination," Anal Chim Acta. 634(1): 89-95.
GCA Saliva-Check Mutans product sheet. 2011. http://www.gcamerica.com/storage/dps_c/GCA_SALIVA-CHECK_MUTANS-iPad.pdf retrieved Sep. 21, 2019.
International Search Report and Written Opinion dated Nov. 30, 2021, in PCT Application No. PCT/US2021/046166.
JP 2nd Office Action dated Aug. 30, 2021 issued in JP 2018-511707.
JP 2nd Office Action dated Feb. 3, 2020 issued in JP 2016-573716.
JP Office Action dated Feb. 8, 2019 issued in JP 2016-573716.
JP Office Action dated May 17, 2021 issued in JP 2018-564267.
JP Office Action dated Sep. 7, 2020 issued in JP 2018-511707.
Jue et al. (2014) "Simultaneous Concentration and Detection of Biomarkers on Paper," published document for the Capstone Design team, MicroTAS Annual Meeting, San Antonio, Texas, 7 pages.
Jue et al. (2014) "Using an aqueous two-phase polymer-salt system to rapidly concentrate viruses for improving the detection limit of the lateral-flow immunoassay," Biotechnology and Bioengineering 111(12): 2499-2507.
Jue et al. "Simultaneous Concentration and Detection of Biomarkers on Paper," document submitted but not published, UCLA, 23 pages.
Kim, et al. (2013) "Image Analysis of a Lateral Flow Strip Sensor for the Detection of *Escherichia coli* 0157:H7." J. of Biosystems Eng. 38(4):335-340.
Koczula, et al. (2016) "Lateral flow assays." Essays in Biochemistry 60: 111-120.
KR Office Action dated Aug. 23, 2021 issued in KR 10-2019-7000413.
KR Office Action dated Mar. 22, 2021 issued in KR 10-2016-7027705.
Leung et al. (2008) "InfectCheck CRP barcode-style lateral flow assay for semi-quantitative detection of C-reactive protein in distinguishing between bacterial and viral infections," J Immunol Meth. 336(1): 30-36.
Luo, et al. (2005) "PDMS microfludic device for optical detection of protein immunoassay using gold nanoparticles." Lab on a Chip 5:726-729.

(56) References Cited

OTHER PUBLICATIONS

Mashayekhi et al. (2009) "Concentration of mammalian genomic DNA using two-phase aqueous micellar systems," Biotechnology and Bioengineering 102(6): 1613-1623, publ online Nov. 3, 2008, publ in journal Apr. 15, 2009.
Mashayekhi et al. (2012) "Enhancing the lateral-flow immunoassay for detection of proteins using an aqueous two-phase micellar system," Anal. Bioanal. Chem. 404: 2057-2066.
Mashayekhi F., et al., "Enhancing the Lateral-flow Immunoassay for Viral Detection Using an Aqueous Two-phase Micellar System", Analytical and Bioanalytical Chemistry, (Sep. 24, 2010), vol. 398, No. 7, pp. 2955-2961.
McCudden et al. (2012) "Evaluation of high resolution gel beta 2-transferrin for detection of cerebrospinal fluid leak," Clinical Chemistry and Laboratory Medicine 6 pages [Abastract].
McCudden et al. (2013) "Evaluation of high resolution gel β2-transferrin for detection of cerebrospinal fluid leak." Clin. Chem. Lab. Med., 51(2): 311-315, CCLM / FESCC. 0. 1-5. 10.1515/cclm-2012-0408.
Mosley G. et al. (2017) "Improved lateral-flow immunoassays for chlamydia and immunoglobulin M by sequential rehydration of two-phase system components within a paper-based diagnostic" Mikrochimica Acta 184(10): 4055-4064.
MY Office Action dated Dec. 2, 2019 issued in MY PI2016001615.
NIH Small Business Technology Transfer Grant Application, Proposal to improve healthcare of tooth decay by developing a point-of-care (POC) diagnostic device, 6 pages, submitted Nov. 19, 2014.
PCT International Preliminary Report on Patentability dated Dec. 20, 2018 issued in PCT/US2017/036418.
PCT International Preliminary Report on Patentability dated Dec. 3, 2019 issued in PCT/US2018/035204.
PCT International Preliminary Report on Patentability dated Feb. 26, 2019 issued in PCT/US2017/047849.
PCT International Preliminary Report on Patentability dated Mar. 15, 2018 issued in PCT/US2016/050257.
PCT International Preliminary Report on Patentability dated Oct. 1, 2019 issued in PCT/US2018/024392.
PCT International Preliminary Report on Patentability dated Sep. 13, 2016 issued in PCT/US2015/019297.
PCT International Search Report and Written Opinion dated Aug. 3, 2018 issued in PCT/US2018/035204.
PCT International Search Report and Written Opinion dated Dec. 1, 2017 issued in PCT/US2017/047849.
PCT International Search Report and Written Opinion dated Dec. 22, 2016 issued in PCT/US2016/050257.
PCT International Search Report and Written Opinion dated Jun. 15, 2018 issued in PCT/US2018/024392.
PCT International Search Report and Written Opinion dated Jun. 3, 2015 issued in PCT/US2015/019297.
PCT International Search Report and Written Opinion dated Sep. 20, 2017 issued in PCT/US2017/036418.
Pereira et al. (2014) "Enhancing the phase separation behavior of a micellar aqueous two-phase system in a paper-based diagnostic," The Annual UC System wide Bioengineering Symposium, Irvine, California, poster, 1 page.
Pereira et al. (2014) "Enhancing the phase separation behavior of a micellar aqueous two-phase system in a paper-based diagnostic," UC Bioengineering Symposium 2014, Abstract, 2 pages.
Pereira et al. (2014) "Paper-based diagnostic accelerates phase separation of a micellar aqueous two-phase system," The Biomedical Engineering Society Annual Meeting, San Antonio, Texas, poster, 1 page.
Pereira et al. (2015) "Improving malaria biomarker detection and accelerating micellar two-phase separation with a paper-based diagnostic," Department of Engineering, UCLA 90095, UCLA Tech Forum, abstract, 1 page.
Pereira et al. (2015) "Improving malaria biomarker detection and accelerating micellar two-phase separation with a paper-based diagnostic," The UCLA Engineering Tech Forum, Los Angeles, California, poster, 1 page.
Pereira et al. (2015) "Single-step, paper-based concentration and detection of a malaria biomarker," Analytica Chimica Acta 882: 83-89.
Pereira et al. "Paper-based diagnostic accelerates phase separation of a micellar aqueous two-phase system," Department of Engineering, University of California, Los Angeles, abstract, 2 pages.
Phase Diagnostics, Business Plan, OneStart Competition 2015, May 2015, 12 pages.
Risch, et al. (2005) "Rapid, accurate and non-invasive detection of cerebrospinal fluid leakage using combined determination of β-trace protein in secretion and serum" Clinica Chimica Acta 351: 169-176.
Sampaio et al. (2009) "Predictability of quantification of beta-trace protein for diagnosis of cerebrospinal fluid leak: Cutoff determination in nasal fluids with two control groups." Am. J. Rhinol. Allerg. 23(6): 585-590.
SG Examination Report dated May 14, 2019 issued in SG 11201607582R.
SG Office Action [Search Report and Written Opinion] dated Jan. 24, 2018 issued in SG 11201607582R.
Song, et al. (2016) "Instrument-Free Point-of-Care Molecular Detection of Zika Virus." Analytical Chemistry 88: 7289-7294.
U.S. Final Office Action dated Jun. 1, 2021 issued in U.S. Appl. No. 15/756,542.
U.S. Final Office Action dated Jun. 4, 2020 issued in U.S. Appl. No. 15/756,542.
U.S. Final Office Action dated May 17, 2021 issued in U.S. Appl. No. 16/498,312.
U.S. Notice of Allowance dated Apr. 3, 2019 issued in U.S. Appl. No. 15/990,398.
U.S. Notice of Allowance dated Aug. 23, 2021 issued in U.S. Appl. No. 16/498,312.
U.S. Notice of Allowance dated Aug. 8, 2017 issued in U.S. Appl. No. 14/641,022.
U.S. Notice of Allowance dated Feb. 28, 2018 issued in U.S. Appl. No. 15/787,638.
U.S. Notice of Allowance dated Jan. 12, 2022, in U.S. Appl. No. 16/326,687.
U.S. Notice of Allowance dated Jul. 20, 2017 issued in U.S. Appl. No. 14/641,022.
U.S. Notice of Allowance dated Nov. 16, 2021 issued in U.S. Appl. No. 15/756,542.
U.S. Office Action Advisory Action dated Aug. 20, 2021 issued in U.S. Appl. No. 15/756,542.
U.S. Office Action Advisory Action (second) dated Sep. 17, 2021 issued in U.S. Appl. No. 15/756,542.
U.S. Office Action dated Jan. 21, 2021 issued in U.S. Appl. No. 15/756,542.
U.S. Office Action dated Jan. 6, 2017 issued in U.S. Appl. No. 14/641,022.
U.S. Office Action dated Jun. 4, 2021 issued in U.S. Appl. No. 16/326,687.
U.S. Office Action dated Jun. 9, 2021 issued in U.S. Appl. No. 16/307,125.
U.S. Office Action dated Nov. 2, 2018 issued in U.S. Appl. No. 15/990,398.
U.S. Office Action dated Oct. 27, 2020 issued in U.S. Appl. No. 16/498,312.
U.S. Office Action dated Sep. 26, 2019 issued in U.S. Appl. No. 15/756,542.
U.S. Office Action [Restriction Requirement] dated May 14, 2019 issued in U.S. Appl. No. 15/756,542.
U.S. Restriction Requirement dated Jan. 25, 2022, in U.S. Appl. No. 16/616,923.
Wong et al. (2015) "Direct Reading of Bona Fide Barcode Assays for Diagnostics with Smartphone Apps," Scientific Reports 5, Article No. 11727 (11 pages).
Wu et al. (Jul. 21, 2014) "Research highlights: increasing paper possibilities" Lab on a Chip, 14(17) 3258-3261.
Yu, et al. (2009) "Flow-through functionalized PDMS microfluidic channels with dextran derivative for ELISAs." Lab on a Chip 9:1243-1247.
AU Office Action dated Oct. 10, 2022, in Application No. AU2016318103.

(56) References Cited

OTHER PUBLICATIONS

CA Office Action dated Jan. 28, 2023, in Application No. CA3002020.
CA Office Action dated May 19, 2022, in Application No. CA3002020.
CN Fourth Office Action dated Mar. 24, 2022 issued in CN 201680059385.6 with English translation.
CN Office Action dated Aug. 29, 2022 in Application No. CN201780046652 with English translation.
CN Office Action dated Dec. 15, 2022 in Application No. 201880042214.1 with English translation.
CN Office Action dated Feb. 24, 2022, in Application No. CN201780046652 with English translation.
European Office Action dated Mar. 9, 2023 in Application No. EP18809609.3.
International Preliminary Report on Patentability dated Mar. 2, 2023, in PCT Application No. PCT/US2021/046166.
JP Office Action dated Dec. 12, 2022, in Application No. 2018-564267 with English translation.
JP Office Action dated Apr. 3, 2023 in Application No. JP2022-28070 with English translation.
JP Office Action dated Aug. 8, 2022, in Application No. JP2021-15690 with English translation.
JP Office Action dated Feb. 14, 2022, in Application No. JP2021-15690 with English translation.
JP Office Action dated Mar. 7, 2022, in Application No. JP2018-564267 with English translation.
KR Office Action dated Apr. 26, 2023, in Application No. KR10-2019-7000413 with English translation.
KR Office Action dated Jan. 25, 2022, in Application No. KR1020167027705 with English translation.
KR Office Action dated Jan. 26, 2023, in Application No. KR10-2018-7009424 with English translation.
KR Office Action dated Jun. 21, 2022, in Application No. KR10-2019-7000413 with English translation.
Le, A.M., et al., "Improving the Lateral-Flow Immunoassay Using Aqueous Two-Phase Systems", 2012, pp. 78 pages.
Raja, S. et al., "Aqueous Two Phase Systems for the Recovery of Biomolecules—A Review", Science and Technology, 2011, vol. 1, No. 1, pp. 7-16.
Sarangi, B.K. et al., "Purification of Alkaline Protease from Chicken Intestine by Aqueous Two Phase System of Polyethylene Glycol and Sodium Citrate", Journal of Food Science and Technology, Nov. 1, 2010, vol. 48, No. 1, pp. 36-44.
U.S. Final office Action dated Jun. 23, 2022 in U.S. Appl. No. 16/307,125.
U.S. Final Office Action dated Mar. 10, 2023 in U.S. Appl. No. 16/616,923.
U.S. Non-Final Office Action dated Jun. 24, 2022, in U.S. Appl. No. 16/616,923.
U.S. Non-Final Office Action dated Mar. 29, 2023 in U.S. Appl. No. 17/673,530.
U.S. Non-Final Office Action dated May 25, 2022, in U.S. Appl. No. 16/751,114.
U.S. Notice of Allowance dated Dec. 13, 2022 in U.S. Appl. No. 16/751,114.

\* cited by examiner

SEMI-QUANTITATIVE LATERAL-FLOW IMMUNOASSAY FOR THE DETECTION OF CSF LEAKS

CROSS-REFERENCE TO RELATED APPLICATIONS

This application is a continuation of U.S. Ser. No. 16/498,312, filed on Sep. 26, 2019, which is a U.S. 371 National Phase of PCT/US2018/024392, filed on Mar. 26, 2018, which claims benefit of and priority to U.S. Ser. No. 62/477,230, filed on Mar. 27, 2017, each of which is incorporated herein by reference in its entirety for all purposes.

STATEMENT OF GOVERNMENTAL SUPPORT

This invention was made with government support under Grant Number NS099800, awarded by the National Institutes of Health. The Government has certain rights in the invention.

BACKGROUND

Cerebrospinal fluid (CSF) leak is a common complication of numerous procedures in otolaryngology. It has been estimated that up to 13.8% of endoscopic skull base surgeries result in CSF leaks. In the acute setting, diagnostic options are limited. These include imaging techniques such as magnetic resonance imaging (MRI) or computer tomography (CT) or taking the patient directly to the operating room for management. This is largely guided by the surgeon's discretion and clinical intuition. These imaging modalities are costly and some expose the patient to radiation. They also do not always identify a site of leak when one exists. Alternatively, operative management is also an expensive process that exposes the patient to general anesthesia and other perioperative risks. This involves identifying the site of the leak and using either native tissue or biocompatible materials to patch the affected site.

Clinicians and surgeons need a quick, reliable and affordable test to help identify CSF leaks in the outpatient or postoperative settings. It is often difficult to distinguish normal nasal and otologic secretions from those containing CSF as they may be similar in appearance. This distinction remains important because failure to recognize and repair a leak can result in severe complications, such as meningitis, brainstem herniation, and death. Currently, there are no proven, available tests that allow a physician concerned about a CSF leak to inexpensively and non-invasively rule out the presence of a leak. Alternative methods have been developed for the detection of CSF leaks, such as beta-2 transferrin electrophoresis or enzyme-linked immunosorbent assay (ELISA), however they are rarely used due to high cost and long time-to-result (often multiple days). If a patient has a CSF leak, a test that takes days to return is far too long. The patient can develop meningitis or brain herniation in that amount of time.

SUMMARY

There is a great and urgent clinical need for a quick, reliable and affordable test to help identify CSF leaks in the outpatient or postoperative settings. Recently, researchers have looked into the detection of beta-trace protein (βTP) using a nephelometric assay and found it to be comparable to beta-2 transferrin in sensitivity and specificity for CSF. Although used in a research setting, this technique has yet to be utilized in the clinical setting.

In various embodiments devices and methods for determining the presence (or absence) of a cerebrospinal fluid (CSF) leak are provided. In certain embodiments the devices utilize a semi-quantitative, barcode-style lateral-flow immunoassay (LFA) that quantifies the level of beta-trace protein (βTP) in a sample.

Various embodiments contemplated herein may include, but need not be limited to, one or more of the following:

Embodiment 1: A lateral flow device for the semi-quantitative detection of a cerebrospinal fluid leak, said device comprising:
  a porous substrate;
  a sample addition zone disposed on or in said porous substrate; a detection zone disposed on or in said porous substrate where said detection zone comprises at least a first test line (T1) and a second test line (T2) each test line comprising binding moieties that bind a complex formed between beta-trace protein (βTP) and an indicator attached to a βTP binding molecule;
  wherein said porous substrate defines a flow path through which a sample applied to the sample addition zone flows under capillary action away from said sample addition zone into said detection zone; and wherein
  said first test line (T1) and said second test line (T2) are is configured so that either no test line signal or just a signal at the first test line (T1) is detectable when βTP concentration in a sample applied to said device is lower than the βTP level indicative of a CSF leak; and
  said second test line (T2) is configured so that a signal is detectable at said second test line when βTP concentration in a sample applied to said device is greater than the βTP level indicative of a CSF leak.

Embodiment 2: The device of embodiment 1, wherein said first test line (T1) and said second test line (T2) are configured so that either no test line signal or just a signal at said first test line (T1) is detectable when βTP concentration in a sample applied to said device is lower than about 1.3 mg/L in a nasal drip sample.

Embodiment 3: The device of embodiment 2, wherein said first test line (T1) is configured so that a signal is detectable at said first test line when βTP concentration in a sample applied to said device is greater than about 0.7 mg/L, or greater than about 0.8 mg/L, or greater than about 0.9 mg/L, or greater than about 1.0 mg/L, or greater than about 1.1 mg/L, or greater than about 1.2 mg/L, or at or greater than 1.3 mg/L in a nasal drip sample.

Embodiment 4: The device according to any one of embodiments 1-3, wherein said first test line (T1) and said second test line (T2) are configured so that a signal is detectable at both test lines when βTP concentration in a sample applied to said device is greater than about 1.3 mg/L.

Embodiment 5: A lateral flow device for the semi-quantitative detection of a cerebrospinal fluid leak, said device comprising:
  a porous substrate;
  a sample addition zone disposed on or in said porous substrate; a detection zone disposed on or in said porous substrate where said detection zone comprises at least a first test line (T1), a second test line (T2), and a third test line (T3), each test line comprising binding moieties that bind a complex formed between beta-trace protein (βTP) and an indicator attached to a βTP binding molecule;
  wherein said porous substrate defines a flow path through which a sample applied to the sample addition zone flows under capillary action away from said sample addition zone into said detection zone; and wherein said first test line (T1) said second test line (T2) and said third test line (T3) are configured so that either no test line signal or just a signal at said first test line (T1) is detectable when βTP concentration in a sample applied to said device is lower than or equal to the βTP level indicative of the absence of a CSF leak;

said first test line (T1) said second test line (T2) and said third test line (T3) are configured so that a signal is detectable at said first test line and said second test line, but not at said third test line when βTP concentration in a sample applied to said device is greater than the βTP level indicative of no CSF leak and less than a βTP level definitive of the presence of a CSF leak; and a signal is detectable at all three test lines T1, T2, and T3 when βTP concentration in a sample applied to said device is equal to or greater than a βTP level definitive of the presence of a CSF leak.

Embodiment 6: The device of embodiment 5, wherein said first test line (T1) said second test line (T2) and said third test line (T3) are configured so that no signal is detectable at test lines T1, T2, or T3, or a signal is detectable only at test line T1, when βTP concentration is less than about 0.7 mg/L in a nasal drip sample applied to said device.

Embodiment 7: The device according to any one of embodiments 5-6, wherein said first test line (T1) said second test line (T2) and said third test line (T3) are configured so a signal is detectable at test lines T1, and T2, but not at test line T3, when βTP concentration ranges from about 0.7 mg/L up to about 1.3 mg/L in a nasal drip sample applied to said device.

Embodiment 8: The device according to any one of embodiments 5-7, wherein said first test line (T1) said second test line (T2) and said third test line (T3) are configured so a signal is detectable at test lines T1, T2, and T3, when βTP concentration is greater than about 1.3 mg/L in a nasal drip sample applied to said device.

Embodiment 9: The device according to any one of embodiments 1-8, wherein said lateral flow device comprise a control line downstream from said first test line and said second test line, wherein said control line comprises binding moieties that secondary antibody that can capture the said indicator, in the presence or absence of βTP.

Embodiment 10: The device according to any one of embodiments 1-9, wherein said lateral flow device comprises a conjugation zone comprising said indicator attached to a βTP binding molecule, where said conjugation zone is disposed in said sample addition zone and/or between said sample addition zone and said detection zone, wherein said conjugation zone contains said indicator attached to a βTP binding molecule.

Embodiment 11: The device according to any one of embodiments 1-10, wherein said lateral flow device comprises an absorbent pad disposed downstream from said detection zone and when said control line is present said absorbent pad is disposed downstream from said control line.

Embodiment 12: The device according to any one of embodiments 1-11, wherein said porous substrate is disposed on a backing.

Embodiment 13: The device of embodiment 12, wherein said backing substantially fluid impermeable.

Embodiment 14: The device according to any one of embodiments 1-13, wherein said porous substrate is disposed in a cassette that provides a protective covering and permits delivery of a sample to said sample addition zone, and visualization of the test lines in the detection zone, and when present visualization of the control line.

Embodiment 15: The device according to any one of embodiments 1-14, wherein said indicator is selected from the group consisting of a colorimetric indicator, a fluorescent indicator, a radioactive indicator, and a magnetic indicator.

Embodiment 16: The device of embodiment 15, wherein said indicator is a colorimetric indicator.

Embodiment 17: The device of embodiment 16, wherein said indictor comprises a colorimetric indicator selected from the group consisting of a dye, a nanoparticle, and a quantum dot.

Embodiment 18: The device of embodiment 17, wherein said indictor comprises a gold nanoparticle.

Embodiment 19: The device according to any one of embodiments 1-18, wherein said βTP binding molecule comprises a moiety selected from the group consisting of an antibody, a lectin, a protein, a glycoprotein, a nucleic acid, a small molecule, a polymer, a lipid, and combinations thereof.

Embodiment 20: The device of embodiment 19, wherein said βTP binding molecule is an antibody or antibody fragment.

Embodiment 21: The device of embodiment 20, wherein said βTP binding molecule is an antibody that specifically binds βTP.

Embodiment 22: The device according to any one of embodiments 1-21, wherein said binding moieties that bind a complex formed between beta-trace protein (βTP) and an indicator comprise a moiety selected from the group consisting of an antibody, a lectin, a protein, a glycoprotein, a nucleic acid, a small molecule, a polymer, a lipid, and combinations thereof.

Embodiment 23: The device of embodiment 22, wherein said binding moieties that bind a complex formed between beta-trace protein (βTP) and an indicator is an antibody or antibody fragment.

Embodiment 24: The device of embodiment 23, wherein said binding moieties that bind a complex formed between beta-trace protein (βTP) and an indicator is an antibody that specifically binds βTP.

Embodiment 25: The device according to any one of embodiments 1-24, wherein said device is configured to perform a sandwich assay.

Embodiment 26: The device according to any one of embodiments 1-25, wherein said porous substrate comprise a material selected from the group consisting of sintered glass or sintered ceramic, a mineral, cellulose, a fiberglass, a nitrocellulose, polyvinylidene fluoride, a nylon, a charge modified nylon, a polyethersulfone, and combinations thereof.

Embodiment 27: The device of embodiment 26, wherein said porous substrate comprises nitrocellulose.

Embodiment 28: A method of determining the presence of a cerebrospinal fluid (CSF) leak in a subject, said method comprising: applying a biological sample obtained from said subject to a the sample application zone of a device according to any one of clams 1-27; operating said device in a lateral-flow assay format and detecting a signal if present at test lines T1 and T2 in a device comprising two test lines and at test lines T1, T2, and T3 in a device comprising three test lines; and\where there is no detectable signal at any test line or a detectable signal at only at test line T1, identifying the subject as a subject having no CSF leak; where the device comprises two test lines and there is a detectable signal at both test lines T1 and T2 identifying the subject as having a CSF leak; where the device comprises three test lines and there is a detectable signal at all three test lines T1, T2, and T3, identifying the subject as having a CSF leak; where the device comprises three test lines and there is a detectable signal only two test lines T1 and T2, identify the subject as in a indeterminate with respect to CSF leaks and requiring further follow up.

Embodiment 29: The method of embodiment 28, wherein said device is a lateral flow device containing two test lines.

Embodiment 30: The method of embodiment 28, wherein said device is a lateral flow device containing three test lines.

Embodiment 31: The method according to any one of embodiments 28-30, wherein said device does not comprise a conjugation zone and said indicator is combined with said sample before application to said device.

Embodiment 32: The method according to any one of embodiments 28-30, wherein said device comprises a conjugation zone and said sample is applied to said device, without addition of said indicator to said sample.

Embodiment 33: The method according to any one of embodiments 28-32, wherein said sample is diluted prior to application to said device.

Embodiment 34: The method according to any one of embodiments 28-33, wherein said sample is diluted with phosphate-buffered saline (PBS).

Embodiment 35: The method according to any one of embodiments 28-34, wherein said subject is a human.

Embodiment 36: The method according to any one of embodiments 28-34, wherein said subject is a non-human mammal.

Embodiment 37: The method according to any one of embodiments 28-36, wherein said subject is a post-surgical subject.

Embodiment 38: The method of embodiment 37, wherein said subject has had scalp or neurosurgery.

Embodiment 39: The method according to any one of embodiments 28-38, wherein said biological sample comprise a nasal drip sample and/or a serum sample.

Embodiment 40: The method according to any one of embodiments 28-39, wherein said method comprises determining βTP in a nasal drip sample from said subject and determining βTP in a serum sample of said subject.

Embodiment 41: The method of embodiment 40, wherein said method comprises determining the nasal drip to serum βTP concentration ratio.

Embodiment 42: The method of embodiment 41, wherein a ratio of <2 is classified as negative for the presence of CSF and a ratio of >2 is classified as positive for a CSF leak.

Embodiment 43: A kit for semi-quantification of βTP in a biological sample, said kit comprising a container containing a lateral flow device for the semi-quantitative detection of a cerebrospinal fluid leak according to any one of embodiments 1-27.

Embodiment 44: The kit of embodiment 43, wherein said kit contains two barcode-style LFA test devices, one for testing serum and the other for testing a nasal drip sample.

Embodiment 45: The kit according to any one of embodiments 43-44, wherein said kit comprises a reference card that correlates the number and intensity of visible test lines with the concentrations of βTP in the sample.

Embodiment 46: The kit according to any one of embodiments 43-45, wherein said kit further comprise a smartphone LSA reader for said device.

Embodiment 47: The kit according to any one of embodiments 43-46, wherein said kit comprises instructions for using said kit for semi-quantification of βTP in a biological sample.

Embodiment 48: A smartphone-based LFA reader for reading the test lines on a device according to any one of embodiments 1-27.

Embodiment 49: The reader of embodiment 48, wherein said reader is configured to photograph the test strips on said lateral flow assay device in a controlled light setting.

Embodiment 50: The reader of embodiment 49, wherein said device converts said photographs the photos to grayscale, locates the test lines on the LFA device by searching for peaks in pixel intensity.

Embodiment 51: The reader of embodiment 50, wherein said device determines the mean or median grayscale intensity of each line and, optionally, the sum of all test line intensities.

Embodiment 52: The reader of embodiment 51, wherein said device compares the measured line intensities with an internal standard curve and displays the concentration of βTP in the sample and/or a clinical diagnosis.

Definitions

The terms "subject," "individual," and "patient" may be used interchangeably and typically a mammal, in certain embodiments a human or a non-human primate. While the devices and methods are described herein with respect to use in humans, they are also suitable for animal, e.g., veterinary use. Thus certain illustrative organisms include, but are not limited to humans, non-human primates, canines, equines, felines, porcines, ungulates, lagomorphs, and the like. Accordingly, certain embodiments contemplate the devices and methods described herein for use with domesticated mammals (e.g., canine, feline, equine), laboratory mammals (e.g., mouse, rat, rabbit, hamster, guinea pig), and agricultural mammals (e.g., equine, bovine, porcine, ovine), and the like. The term "subject" does not require one to have any particular status with respect to a hospital, clinic, or research facility (e.g., as an admitted patient, a study participant, or the like). Accordingly, in various embodiments, the subject can be a human (e.g., adult male, adult female, adolescent male, adolescent female, male child, female child) under the care of a physician or other health worker in a hospital, psychiatric care facility, as an outpatient, or other, clinical context. In certain embodiments, the subject may not be under the care or prescription of a physician, or other, health worker.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fvs (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons. The important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405 and 4,956,778). Particularly preferred antibodies should include all that have been displayed on phage (e.g., scFv, Fv, Fab and disulfide linked Fv) (Reiter et al. (1995) *Protein Eng.* 8: 1323-1331).

The term "biological sample" refers to sample is a sample of biological tissue, cells, or fluid that, in a healthy and/or pathological state, is may contain CSF in a subject that has a CSF leakage. Illustrative samples include, but are not limited to blood or plasma samples, nasal and/or oral fluid samples, and the like. Although the sample is typically taken from a human patient, the assays can be used to detect CSF in samples from any mammal, such as dogs, cats, sheep, cattle, and pigs, etc. The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used and the term sample is intended to include pre-treated samples as well as acute samples.

The phrase a "signal is detectable at a test line" or detectable at a control line means a signal indicative of the present of the moiety of interest at the test line. For example, where the signal is a colorimetric signal the signal is detectable if visible with the naked eye or detected using a reader device for the lateral flow assay.

The term "downstream" when used with reference to a lateral flow device indicates that the downstream location is further along the lateral flow device in the direction of fluid flow (capillary flow) than another location. Thus, if location 2 is downstream from location 1, then fluid flowing through the lateral flow device will reach location 1 before reaching location 2.

As used herein, the term "instructions for using said kit for semi-quantification of βTP in a biological sample" includes instructions for using the reagents contained in the kit for the detection and/or semiquantification of βTP. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510 (k) procedure. Information required in an application under 510 (k) includes: 1) The in vitro diagnostic product name, including the trade or proprietary name, the common or usual name, and the classification name of the device; 2) The intended use of the product; 3) The establishment registration number, if applicable, of the owner or operator submitting the 510 (k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510 (k) summary of the safety and effectiveness data upon which the substantial equivalence determination is based; or a statement that the 510 (k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

DETAILED DESCRIPTION

In various embodiments devices and methods are provided for the rapid detection of cerebrospinal fluid (CSF) leaks in a subject. The devices and methods provide a rapid, robust, easy-to-use, and inexpensive point-of-care diagnostic device that can distinguish between samples containing CSF and those that do not.

The current standards for diagnosing CSF leaks include invasive and expensive techniques such as CT and MRI, as well as ELISA and beta-2 transferrin electrophoresis, which are rarely used due to their high cost and long time-to-result. More recently, researchers have looked into the detection of beta-trace protein (βTP) using a nephelometric assay. While rapid and highly sensitive, the βTP nephelometric assay still requires expensive equipment found in a centralized laboratory and extensive training.

The devices described herein provide the ability to rapidly quantify the concentration of βTP in a sample in order to determine the presence or absence of a CSF with the use of a barcode-style lateral flow assay (LFA). This technology can allow for the rapid diagnosis of a CSF leak without the need for expensive equipment, invasive tests, or extensive training. Moreover the devices and methods facilitate rapid detection of a CSF leak before the subject decompensates as a consequence of the leakage.

Accordingly the methods and devices described herein are directed to the detection of βTP in a subject (e.g., in a biological sample derived from a subject). In particular embodiments, lateral-flow assay devices (e.g., bar-code lateral flow devices) are provided for the detection and semi-quantitative determination of CSF in a sample thereby permitting the diagnosis of CSF leaks in a subject. It is noted that, to the extent that the following description is of a specific embodiment or a particular uses, it is intended to be illustrative only, and not limiting of the claimed invention. The following description is intended to cover all alternatives, modifications and equivalents that are included in the spirit and scope of the invention, as defined in the claims.

Lateral flow immunoassays are simple tests for rapid detection of the presence or absence of a target analyte in a sample for home testing, point of care testing, or laboratory applications. "Bar-code" or "ladder" lateral flow immunoassay provides a semi-quantitative measurement of the amount of analyte present in a sample typically by providing multiple detection bands (e.g., in a detection zone) zone each of which represents a different analyte concentration range.

Lateral flow test strips typically utilize a solid support through which a mobile phase (e.g., a liquid sample) can flow through by capillary action to a reaction matrix where a detectable signal, such as color changes or color differences on the test strip, may be generated to indicate the presence or absence of the target analyte. As used herein, the term "capillary action" or "capillarity" means the process by which a molecule is drawn across the lateral test strip due to such properties as surface tension and attraction between molecules.

Figure 1:
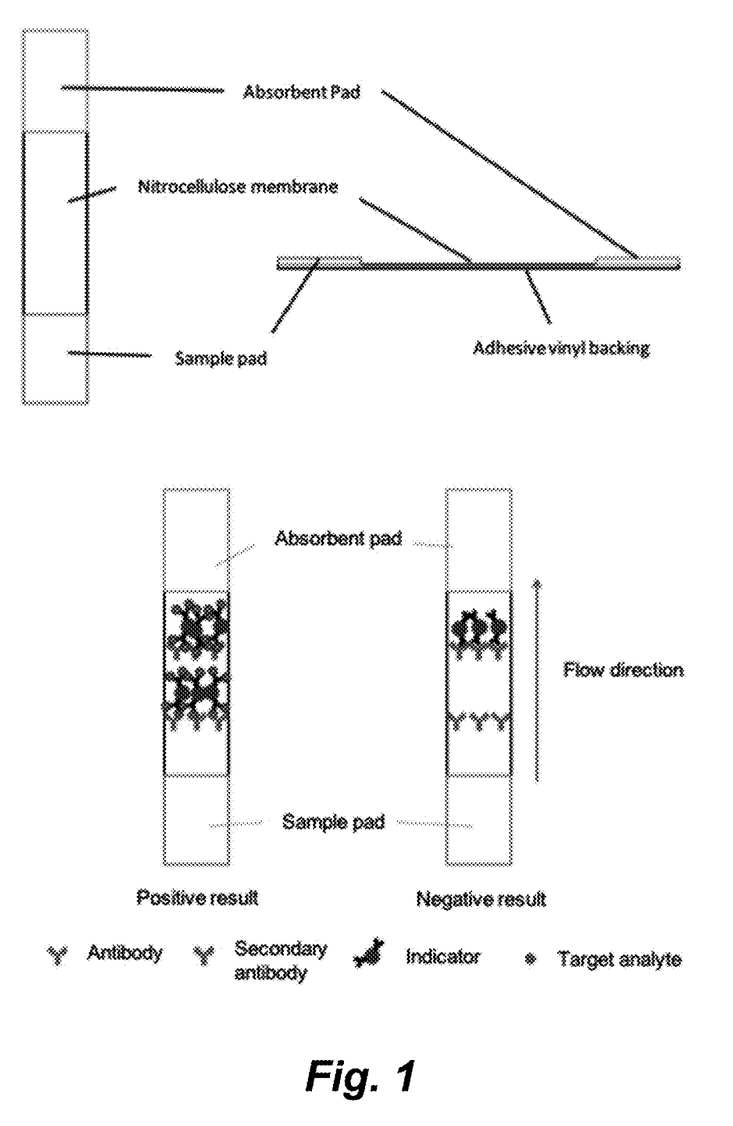
FIG. 1 illustrates a schematic of a typical lateral-flow immunoassay test strip (top). The sandwich format of the lateral-flow immunoassay is illustrated in the bottom panel.

In certain embodiments the concentration of βTP in a sample is quantified using a barcode-style lateral-flow immunoassay (LFA) in order to detect (e.g., determine the presence of or absence of, or severity of) a CSF leak. A typical LFA consists of at least 3 components: a sample pad where the sample is applied to the test strip, a detection zone where there is binding and where results can be observed, and an absorbent pad which acts as a sink for excess sample (FIG. 1, top). In certain embodiments of a sandwich assay format, the LFA indicator (which can be colorimetric, fluorescent, radioactive, etc.) decorated with binding molecules (e.g., antibodies, aptamers, etc.) can be first added to the sample which is then applied to the LFA device. Alternatively, in certain embodiments the LFA comprise a conjugation zone containing the indicator attached to binding molecules and combination of the sample with the indicator can occur in the conjugation zone. If the target, in this case βTP, is present, it will bind to the indicator decorated with the binding molecule. These complexes are flow through the strip into the detection zone towards the absorbent pad when present. If βTP is present, they associate with the binding molecules immobilized on the test line(s) and become sandwiched between the indicator and the membrane providing a signal at the particular test line(s). For example, if the indicator is colorimetric, the colorimetric indicator will exhibit a strong color, and a visual band forms as the βTP-indicator complex accumulates at the test line, indicating a positive result. Alternatively, if no βTP is present, the indicator does not attach to the test line, and the absence of the test line indicates a negative result. Regardless of the presence of βTP, the binding molecule decorated on the indicator can associate with and accumulate on the control line when a control line is present. A band at the control line signifies that the sample has flowed through the strip, indicating a valid test. In certain embodiments then, a positive result is therefore indicated by two bands, one at the test line and one at the control line, while a negative result is indicated by a single band at the control line (FIG. 1, bottom).

While the traditional LFA gives a qualitative "yes" or "no" readout, a more quantitative device would be instrumental in the accurate diagnosis of a CSF leak, where lower concentrations of βTP are indicative of a negative result, and higher concentrations of βTP are indicative of a positive result for a CSF leak. An alternative format of the LFA that provides a more quantitative output is called the barcode-style or ladder LFA, in which multiple test lines are printed on the detection zone. Each test line will have a cut-off, which is the minimum concentration of βTP in a sample necessary for that test line to become visible. These cut-offs can be adjusted by varying the density of the binding molecule that is immobilized, as well as altering the affinity that binding molecule has for βTP. After running the assay, the number of test lines that are visible on the LFA strip can be correlated with an approximate βTP concentration in the sample and thus a clinical diagnosis.

Accordingly, in certain embodiments, a semi-quantitative LFA assay is provided with two test lines to quantify βTP levels. To develop the two test line assay, an antibody to βTP, the capture antibody, is immobilized on the detection zone of the LFA membrane in two locations: test line 1 (T1), and test line 2 (T2). Previous studies have shown that a βTP concentration of >1.3 mg/L, in a nasal drip sample, is a good indicator of a CSF leak.

Figure 2:
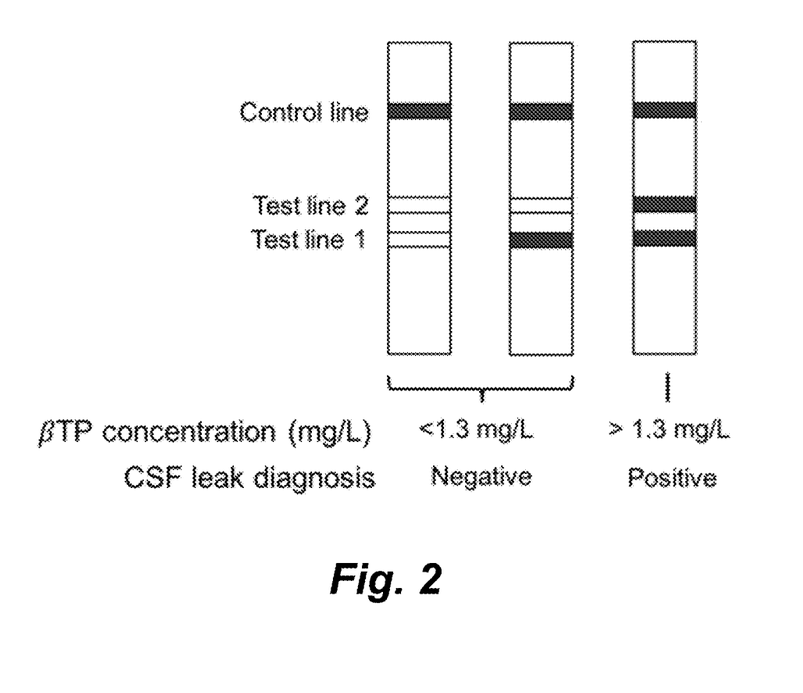
FIG. 2 illustrates a schematic and illustrative βTP cutoff levels of a two-line LFA design.

Accordingly, in certain embodiments, capture moieties (e.g., capture antibodies) are immobilized on the detection zone such that 0 or 1 test line will be detectable (e.g., visible) when the concentration of βTP is below 1.3 mg/L and 2 test lines will be detectable (e.g., visible) when the concentration of βTP is above 1.3 mg/L (FIG. 2). A secondary antibody that can capture the colorimetric indicator, in the presence or absence of βTP, can be immobilized as the control line, downstream from the test lines. In the following example of the two test line barcode-style LFA, gold nanoparticles decorated with anti-βTP antibodies (GNPs) were used as the colorimetric indicator.

In certain embodiments prior to running the assay, the sample is diluted, e.g. 300-fold in phosphate-buffered saline (PBS). The diluted sample is mixed with GNPs and is then applied to the sample pad, where it will begin to flow through the LFA strip. Any βTP in the sample will bind to the GNPs to form DTP-GNP complexes. When these βTP-GNP complexes cross the detection zone, they will first bind to T1. βTP-GNP complexes that do not bind to T1 will be able to bind to T2. Finally, unbound GNPs and any remaining βTP-GNP complexes will bind to the control line to indicate a valid test. After, e.g., 20 minutes, the number of detectable (e.g., visible) test lines is counted. If 0 or 1 test line is present, the sample is considered negative for a CSF leak. If 2 test lines are present, the sample is considered positive for a CSF leak.

Figure 3:
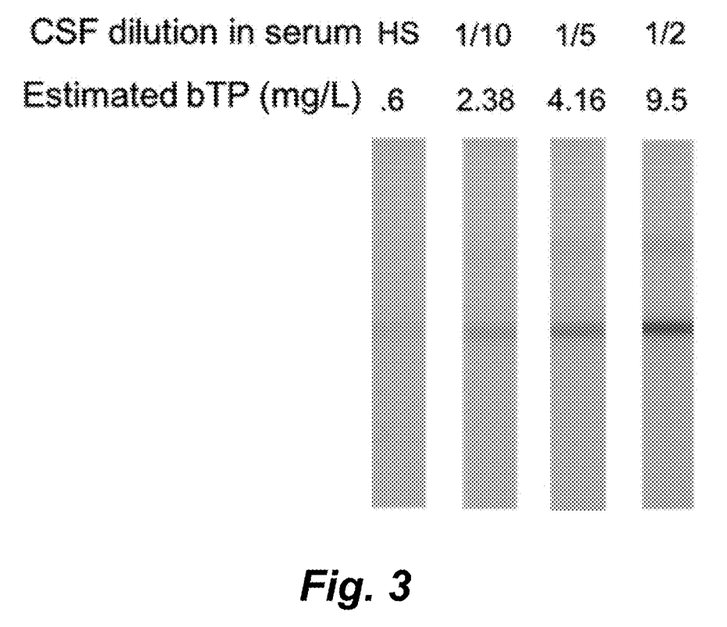
FIG. 3 illustrates dilutions of human CSF in human serum (HS). Negative control, HS, displays 1 visible test line. All tests containing CSF display 2 test lines. There were no control lines printed on these strips.

To demonstrate the two-test line LFA device, a CSF sample obtained from a lumbar drain was diluted in human serum to simulate a clinical nasal drip sample containing trace amounts of CSF. When run on the 2 test line LFA device, all samples containing CSF displayed 2 visible test lines, indicating positive results for the presence of CSF. When the negative control, human serum without CSF, was run, only one test line appeared, indicating a negative result for the presence of CSF (FIG. 3). Control lines were not printed in the results shown.

Figure 4:
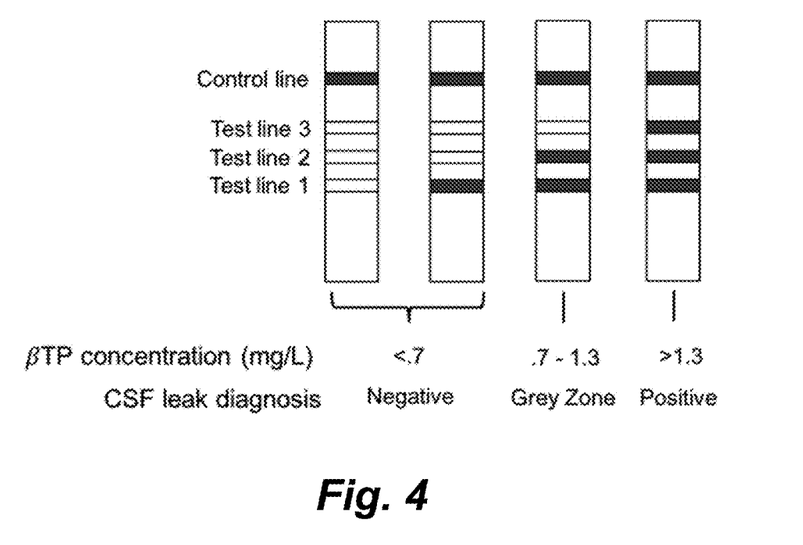
FIG. 4 shows a schematic and illustrative βTP cutoff levels of a three-test line LFA design.

In another illustrative, but non-limiting embodiments, a semi-quantitative LFA device with three test lines to quantify βTP levels is provided. A βTP concentration of >1.3 mg/L has been shown to have relatively high sensitivity when detecting for CSF leaks using the nephelometric assay. However, in the region from 0.7-1.3 mg/L, which we will refer to as a "grey zone", it has been reported that approximately 1 in 3 samples will contain CSF. As a result, if all βTP concentrations of <1.3 mg/L are classified as negative for CSF, potentially life-threatening CSF leaks will be misdiagnosed. Therefore, it is beneficial to develop a device that can identify samples in this grey zone, so that further testing can be performed before ruling out the presence of a CSF leak. To develop this assay, an antibody to βTP, the capture antibody, is immobilized on the detection zone of the LFA membrane in three locations: test line 1 (T1), test line 2 (T2), and test line 3 (T3). The capture moieties (e.g., antibodies) will be immobilized such that 0 or 1 test line will be visible when the concentration of βTP in a sample is below 0.7 mg/L, 2 test lines will be visible when the concentration is 0.7-1.3 mg/L, and 3 test lines will be visible when the concentration is greater than 1.3 mg/L (FIG. 4). A secondary antibody, that can capture the indicator bound with detection antibodies, in the presence or absence of βTP, is immobilized as the control line, downstream from the test lines. In the following example of the three test line barcode-style LFA, gold nanoparticles decorated with anti-βTP antibodies (GNPs) are used as the colorimetric indicator.

In certain embodiments prior to running the assay, the sample to be run is diluted, e.g., 300-fold in phosphate-buffered saline (PBS). The diluted sample is then applied to the sample pad, where it begins to flow through the LFA strip. Any βTP in the sample binds to the GNPs to form βTP-GNP complexes. When these DTP-GNP complexes cross the detection zone, they will first bind to T1. βTP-GNP complexes that do not bind to T1 will be able to bind to T2. βTP-GNP complexes that do not bind to T1 or T2 will then be able to bind to T3. Finally, the unbound GNPs and any remaining βTP-GNP complexes will bind to the control line to indicate a valid test. After, e.g., 20 minutes, the number of colored test lines is counted. If 0 or 1 test line is present, the sample is considered negative for a CSF leak. If 2 test lines are present, the sample is considered in the grey zone, where further testing is required and it is recommended to rerun the assay with a newly collected sample. If 3 test lines are present, the sample is considered positive for a CSF leak.

Another aspect of this invention is the development of a kit that contains two separate LFA tests to quantify the level of βTP in both a patient's serum and nasal drip sample. Previous studies have demonstrated that the ratio of βTP concentrations in nasal drip sample to serum is also a sensitive and specific indicator of the presence or absence of a CSF leak. This invention looks to use the barcode-style LFA to quantify the βTP concentration in both serum and nasal drip samples. In certain embodiments the kit will contain two barcode-style LFA test devices, one for testing serum and the other for testing the nasal drip sample. In certain embodiments it can also contain a reference card that correlates the number and intensity of visible test lines with the concentrations of βTP in the sample. After running a patient's serum and nasal drip samples on their respective LFA test strips and obtaining the βTP concentrations in each samples, the nasal drip to serum βTP concentration ratio will be taken. In certain embodiments a ratio of less than 2 (<2) is classified as negative for the presence of CSF and a ratio of greater than 2 (>2) or greater than or equal to 2 is positive.

Other embodiments contemplated herein involve the integration of a smartphone-based LFA reader with the LFA test strips described above. An optional smartphone-based LFA reader can further improve the ease-of-interpretation and accuracy of the tests for the detection of CSF leaks. Photographs of the LFA test strips are taken (in certain embodiments in a controlled light setting, such as an external photo light box or an integrated phone attachment that blocks outside light and uses the smartphone flash as a lighting source). A smartphone application then converts the photos to grayscale (e.g., 8-bit, 16-bit, 32-bit grayscale). Each test line on the LFA strip can be located by searching for peaks in pixel intensity. Once the location of each test line is determined, the mean grayscale intensity of each line can be calculated and/or as the sum of all test line intensities. The measured intensities can be compared with an internal standard curve and the concentration of βTP in the sample and/or the clinical diagnosis can be displayed on the smartphone screen."

Lateral Flow Assay Components

In various embodiments the lateral flow assay comprises a porous substrate, a sample addition zone disposed on or in the porous substrate; and a detection zone disposed on or in said porous substrate where said detection zone comprises at least a first test line (T1) and a second test line (T2) and in certain embodiments a third test line (T3) as described above. In certain embodiments the lateral flow assay additionally comprises a conjugation zone containing the indicator attached to a moiety that binds βTP. The lateral flow device can additionally comprise a control line and/or an absorbent pad (e.g., sink).

Sample Receiving Zone

The LFA devices described herein typically comprise a sample receiving zone for application of the biological sample to the device. In certain embodiments the sample receiving zone comprise a sample pad disposed on or in the porous substrate. In certain embodiments the sample pad can act as a filter that can remove debris, contaminants, and mucus from the collected fluid. It can also store dried reagents, and when rehydrated, these reagents can (i) adjust the solution for optimal detection conditions (pH, ionic strength, etc); and (ii) break down mucus, glycoproteins, and other viscous materials in the collected specimen that may affect detection. Illustrative materials for the sample pad include, but are not limited to, cellulose, nitrocellulose, fiberglass, cotton, woven or nonwoven paper, etc. Reagents on the pad may include, but are not limited to, surfactants such as Triton X-100, Tween 20, or sodium dodecyl sulfate, etc.; polymers such as polyethylene glycol, poloxamer, polyvinylpyrrolidone (PVP), etc.; buffers such as phosphate-buffered saline, 4-(2-hydroxyethyl)-1-piperazineethanesulfonic acid (HEPES), Tris(hydroxymethyl)aminomethane (Tris), sodium borate, TRICINE, etc.; proteins such as albumin, etc.; enzymes such as protease, etc.; salts such as sodium chloride, sodium phosphate, sodium cholate, potassium phosphate, etc. In various embodiments these reagents can be applied to the sample pad by (i) soaking the paper material in the reagent solution, or (ii) through wicking the membrane via capillary flow. The treated sample pad can be dried by (i) air dry (let sit in room temperature); (ii) baking (place in high temperature using an oven or heating device); (iii) vacuum; or (iv) lyophilization.

Conjugation Zone

Figure 5:
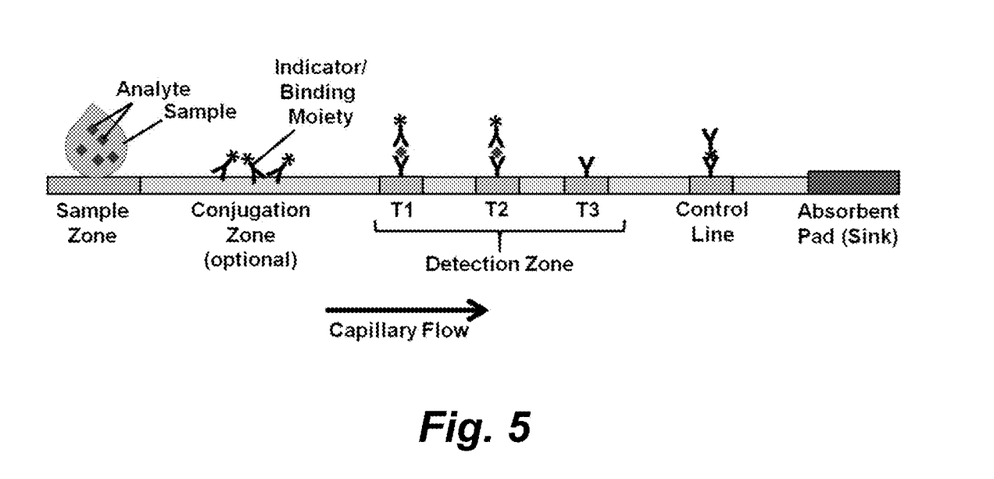
FIG. 5 schematically illustrates a lateral-flow immunoassay incorporating a conjugation zone.

In certain embodiments the LFA devices described herein can comprise a conjugation zone for mixing the sample with an indicator attached to a βTP binding molecule (see, e.g., FIG. 5). In certain embodiments the conjugation zone comprises a conjugate pad. In certain embodiments the conjugation zone, when present can contain dehydrated indicators (e.g., colorimetric indicators, a fluorescent indicators, a radioactive indicators, magnetic indicators, etc.) decorated with binding moieties that bind the βTP target analyte. In certain embodiments the binding moieties are specific binding moieties that have high affinity towards βTP. When the sample solution reaches the conjugate pad, the indicators (e.g., colorimetric indicators) are rehydrated. The binding moieties on the indicators can then bind to the βTP the resulting complexes can flow to the detection zone. In certain embodiments the indicators can comprise colorimetric indicators that can comprise metallic particles such as gold, silver particles, polymeric particles such as latex beads, and polystyrene particles encapsulating visible or fluorescent dyes. Illustrative materials material for the conjugation zone (e.g., conjugate pad) include, but are not limited to, cellulose, nitrocellulose, fiberglass, cotton, woven or nonwoven paper etc. In certain embodiments the colorimetric indicators can be applied and dehydrated onto the pad as described above.

Detection Zone

In certain embodiments the reaction pad, when present, can comprise immobilized reagents, and when the immobilized reagents react with the sample solution, they may produce signals (e.g., visual signals) to indicate the presence or absence or quantity of the target analyte(s) at particular test lines. Illustrative materials for the detection zone include, but are not limited to cellulose, nitrocellulose, fiberglass, cotton, woven or nonwoven paper etc.

In certain embodiments for a lateral-flow test strip, the reagents in the detection zone are immobilized in the form of lines perpendicular to the direction of flow to ensure all samples can interact with the immobilized reagents. The concentrations of the reagents can be optimized to control the signal intensities, and thus, control the sensitivity of the assay. For example, a semi-quantitative assay can be designed by immobilizing multiple lines of the same reagent with various concentrations. Each line therefore will yield signals only when a specific concentration of target biomolecules is reached. The concentration of the target biomolecules can then be interpreted by counting the number of lines that are visible, e.g., as described above.

Absorbent Pad/Sink

In certain embodiments the lateral flow device comprises an absorbent pad disposed downstream from the detection zone and when said control line is present the absorbent pad is disposed downstream from the control line. In certain embodiments the sink, when present, can comprise an absorbent pad that collect excess fluid and prevents backflow which can affect the test performance. Illustrative materials for the sink include, but are not limited to cellulose, nitrocellulose, fiberglass, cotton, woven and nonwoven paper etc.

Lateral Flow Assay (LFA) or Flow-Through (Spot) Assay

As explained above, in certain embodiments, the devices and systems described herein are configured to provide a lateral flow assay (LFA) for detection of the target analyte (βTP) in a sample. The LFA typically comprises a porous matrix into which is disposed sample and assay components, e.g., as described above. The porous matrix is configured to and has porosity sufficient to allow the assay reagents to flow through the porous matrix when the components are in a fluid phase. Such porous LFA devices are can be referred to as paper or paper fluidic devices and these terms are used interchangeably.

The term "paper", as used herein, is not limited to thin sheets from the pulp of wood or other fibrous plant substances although, in certain embodiments the use of such papers in the devices described herein is contemplated. Papers more generally refer to porous materials often in sheet form, but not limited thereto that allow a fluid to flow through.

In some embodiments, the porous matrix is sufficiently porous to allow the assay components and target analyte(s) to flow through the LFA. In some embodiments the porous matrix comprises inter alia a material such as a scintered glass ceramic, a mineral, cellulose, a fiberglass, a nitrocellulose, polyvinylidene fluoride, a nylon, a charge modified nylon, a polyethersulfone, combinations thereof, and the like.

Sandwich Assay

In some embodiments, the LFA is configured to provide or run a sandwich assay (see e.g., FIG. 1, bottom left, in copending PCT Application No: PCT/US2015/019297, filed on Mar. 6, 2015, which is hereby incorporated by reference for the LFA configurations described therein). In some embodiments, the sandwich assay comprises a capture moiety that binds the target analyte. In some embodiments, the device comprises an indicator attached to a moiety that binds to the analyte of interest (βTP). In some embodiments, the indicator comprises a detectable property (colorimetric, fluorescent, radioactive, etc.). In some embodiments, the probe comprises a binding moiety that interacts with the target analyte (e.g. an antibody). In some embodiments, the indicator is added to the sample before application to the device and binds the target analyte to form a probe-analyte complex. In some embodiments, the indicator is combined with the sample in a conjugation zone in the LFA device after the sample is added to the device and binds the target analyte to form a probe-analyte complex.

Indicator-analyte complex flows through the LFA or through the flow-through device towards the absorbent pad. In some embodiments, the target analyte of the indicator-analyte complex binds to the capture moiety. In some embodiments, the capture moiety is immobilized on a test line or a test region (e.g., a test layer in a flow-through device) and the indicator-analyte complex becomes immobilized on the test line or in the test region. In some embodiments, the indicator is colorimetric, and the test line or test region will exhibit a strong color (e.g. detectable signal) as the indicator-analyte complex accumulates at the test line or in the test region, indicating a positive result. In some embodiments, there is no target analyte present in the sample, and the indicator of the indicator-analyte complex does not interact with the capture moiety, and the absence of the test line or signal in the test region indicates a negative result at that test line. In some embodiments, the LFA comprises an indicator capture moiety on a control line (or in a control region, e.g., of a flow-through assay device) that interacts directly with the indicator and/or the binding moiety, and thus, regardless of the presence of the target analyte in the sample, the indicator/binding moiety binds to the probe capture moiety and accumulates on the control line or in the control region. In some embodiments, the indicator capture moiety is a secondary antibody that binds the binding moiety, wherein the binding moiety is a primary antibody that binds that target analyte. In some embodiments, the indicator becomes immobilized and detected on the control line or in the control region, indicating a valid test. In some embodiments, a positive result (e.g. target analyte is present in sample) is indicated by a detectable signal at the test line(s) as described above. In some embodiments, a negative result is indicated by a detectable signal at the control line or in the control region in the absence of test line signal(s) as described above.

Indicators

In certain embodiments the systems and/or devices described herein and/or the methods described herein utilize an indicator, where the indicator comprises a binding moiety that binds the target analyte to form an indicator-analyte complex.

In some embodiments, the indicator comprises a material selected from the group consisting of a synthetic polymer, a metal, a mineral, a glass, a quartz, a ceramic, a biological polymer, a plastic, and combinations thereof. In some embodiments, the indicator comprises a polymer selected from the group consisting of polyethylene, polypropylene, nylon (DELRIN®), polytetrafluoroethylene (TEFLON®), dextran and polyvinyl chloride. In some embodiments, the polyethylene is polyethylene glycol. In some embodiments, the polypropylene is polypropylene glycol. In some embodiments, the indicator comprises a biological polymer selected from the group consisting of collagen, cellulose, and chitin. In some embodiments, the indicator comprises a metal selected from the group consisting of gold, silver, platinum titanium, stainless steel, aluminum, and alloys thereof. In some embodiments, the indicator comprises a nanoparticle (e.g., a gold nanoparticle, a silver nanoparticle, etc.).

In some embodiments, the indicator comprises a detectable label. Detectable labels include any composition detectable by spectroscopic, photochemical, biochemical, immunochemical, electrical, optical, or chemical means. Illustrative useful labels include, but are not limited to, fluorescent nanoparticles (e.g., quantum dots (Qdots)), fluorescent dyes (e.g., fluorescein, texas red, rhodamine, green fluorescent protein, and the like, see, e.g., Molecular Probes, Eugene, Oregon, USA), radiolabels (e.g., $^3$H $^{125}$I, $^{35}$S, $^{14}$C, $^{32}$P, $^{99}$Tc, $^{203}$Pb, $^{67}$Ga, $^{68}$Ga, $^{72}$As, $^{111}$In, $^{113m}$In, $^{97}$Ru, $^{62}$Cu, 641Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{111}$Ag, and the like), enzymes (e.g., horse radish peroxidase, alkaline phosphatase and others commonly used in an ELISA), various colorimetric labels, magnetic or paramagnetic labels (e.g., magnetic and/or paramagnetic nanoparticles), spin labels, radio-opaque labels, and the like.

Alternatively or additionally, the indicator can bind to another particle that comprises a detectable label. In some embodiments, the indicator provide a detectable signal at the detection zone (e.g. test line, control line, test region, control region). In some embodiments, the detectable label/property is selected from the group consisting of a colorimetric label/property, a fluorescent label/property, an enzymatic label/property, a colorigenic label/property and a radioactive label/property. In some embodiments, the indicator comprises a gold nanoparticle and the detectable property is a color. In some embodiments, the color is selected from orange, red and purple.

In some embodiments, the indicator further comprises a coating. In some embodiments, the coating comprises polyethylene glycol or polypropylene glycol. In some embodiments, the coating comprises polypropylene. In some embodiments, the coating comprises polypropylene glycol. In some embodiments, the coating comprises dextran. In some embodiments, the coating comprises a hydrophilic protein. In some embodiments, the coating comprises serum albumin. In some embodiments, the coating has an affinity for the first phase solution or the second phase solution.

Binding Moiety

In some embodiments, the binding moiety is a molecule that binds the target analyte ($\beta$TP). In some embodiments, the binding moiety is a molecule that specifically binds $\beta$TP. In some embodiments, "specifically binds" indicates that the molecule binds preferentially to $\beta$TP or binds with greater affinity to the target analyte than to other molecules. By way of non-limiting example, an antibody will selectively bind to an antigen against which it was raised. Also, by way of non-limiting example, a DNA molecule will bind to a substantially complementary sequence and not to unrelated sequences under stringent conditions. In some embodiments, "specific binding" can refer to a binding reaction that is determinative of the presence of a target analyte in a heterogeneous population of molecules (e.g., proteins and other biologics). In some embodiments, the binding moiety binds to its particular target analyte and does not bind in a significant amount to other molecules present in the sample.

In some embodiments, the binding moiety is selected from the group consisting of an antibody, a lectin, a protein, a glycoprotein, a nucleic acid, monomeric nucleic acid, a polymeric nucleic acid, an aptamer, an aptazyme, a small molecule, a polymer, a lectin, a carbohydrate, a polysaccharide, a sugar, a lipid, and any combination thereof. In some embodiments, the binding moiety is a molecule capable binding pair the target analyte.

In some embodiments, the binding moiety is an antibody or antibody fragment. Antibody fragments include, but are not limited to, Fab, Fab', Fab'-SH, F(ab')$_2$, Fv, Fv', Fd, Fd', scFv, hsFv fragments, single-chain antibodies, cameloid antibodies, diabodies, and other fragments described herein.

In certain embodiments, the binding moiety comprises an aptamer. In some embodiments, the aptamer comprises an antibody-analogue formed from nucleic acids. In some embodiments, the aptamer does not require binding of a label to be detected in some assays, such as nano-CHEM-FET, where the reconfiguration would be detected directly. In some embodiments, the binding moiety comprises an aptazyme. In some embodiments, the aptazyme comprises an enzyme analogue, formed from nucleic acids. In some embodiments, the aptazyme functions to change configuration to capture a specific molecule, only in the presence of a second, specific, analyte.

Sample Collection

In various embodiments the sample to be assayed using the devices and methods described herein comprises a biological sample. Illustrative biological samples include, but are not limited to biofluids such as blood or blood fractions, lymph, nasal or oral fluids, and the like.

Where the biological sample comprises a tissue, in certain embodiments, the tissue may be lysed, homogenized, and/or ground and, optionally suspended in a sample solution. Where the biological sample comprise a biological fluid the fluid may be assayed directly or suspended in a sample solution prior to assay. In certain embodiments the sample solution may act to preserve or stabilize the biological sample or components thereof, and/or may act to extract or concentrate the biological sample or components thereof. In certain embodiments the sample solution may comprise a buffer, optionally containing preservatives, and/or enzymes (protease, nuclease, etc.), and/or surfactants, and/or ATPS components.

In certain embodiments, particular in point-of-care embodiments, the sample may be applied to the assay device immediately or after a modest time interval. In certain embodiments the sample may be delivered to a remote testing facility where the assay is run.

Methods and devices for collecting biological samples are well known to those of skill in the art.

Kits

In certain embodiments a kit for semi-quantification of βTP in a biological sample is provided. In certain embodiments the kits comprise a container containing a lateral flow device for the semi-quantitative detection of a cerebrospinal fluid leak as described herein. In certain embodiments the kit contains two barcode-style LFA test devices as described herein, one for testing serum and the other for testing a nasal drip sample. In certain embodiments the kit comprises a reference card that correlates the number and intensity of visible test lines with the concentrations of βTP in the sample. In certain embodiments the kit further comprises a smartphone LSA reader for the LSA device(s). In certain embodiments the kit comprises one or more sample collection devices (e.g., devices for collecting blood or plasma, or nasal or oral material).

In certain embodiments the kit comprises instructions (instructional materials) for using the kit for semi-quantification of βTP in a biological sample.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A lateral flow device for the semi-quantitative detection of a cerebrospinal fluid (CSF) leak using a nasal drip or otologic sample, said device comprising:
   a porous substrate;
   a sample addition zone disposed on or in said porous substrate;
   a detection zone disposed on or in said porous substrate where said detection zone comprises at least a first test line (T1) and a second test line (T2) each test line comprising binding moieties that bind a complex formed between beta-trace protein (βTP) and an indicator attached to a βTP binding molecule;
   wherein said porous substrate defines a flow path through which a sample applied to the sample addition zone flows under capillary action away from said sample addition zone into said detection zone; and
   wherein when a nasal drip sample diluted 300 fold with phosphate buffered saline is applied to said device:
      said first test line (T1) and said second test line (T2) are configured so that either no test line signal or just a signal at the first test line (T1) is detectable when βTP concentration in a sample applied to said device is lower than the βTP level indicative of a CSF leak; and
      said second test line (T2) is configured so that a signal is detectable at said second test line when βTP concentration in a sample applied to said device is greater than the βTP level indicative of a CSF leak.

2. The lateral flow device of claim 1, wherein said device further comprises a third test line (T3), said third test line comprising binding moieties that bind a complex formed between beta-trace protein (βTP) and an indicator attached to a βTP binding molecule, wherein when a nasal drip sample diluted 300 fold with phosphate buffered saline is applied to said device:
   said first test line (T1) said second test line (T2) and said third test line (T3) are configured so that a signal is detectable at said first test line and said second test line, but not at said third test line when βTP concentration in a sample applied to said device is greater than the βTP level indicative of no CSF leak and less than a βTP level definitive of the presence of a CSF leak; and
   a signal is detectable at all three test lines T1, T2, and T3 when βTP concentration in a sample applied to said device is equal to or greater than a βTP level definitive of the presence of a CSF leak.

3. The device of claim 2, wherein said first test line (T1) said second test line (T2) and said third test line (T3) are configured so that no signal is detectable at test lines T1, T2, or T3, or a signal is detectable only at test line T1, when βTP concentration is less than about 0.7 mg/L in a nasal drip sample applied to said device.

4. The device of claim 2, wherein said first test line (T1) said second test line (T2) and said third test line (T3) are configured so a signal is detectable at test lines T1, and T2, but not at test line T3, when βTP concentration ranges from about 0.7 mg/L up to about 1.3 mg/L in a nasal drip sample applied to said device.

5. The device of claim 2, wherein said first test line (T1) said second test line (T2) and said third test line (T3) are configured so a signal is detectable at test lines T1, T2, and T3, when βTP concentration is greater than about 1.3 mg/L in a nasal drip sample applied to said device.

6. The device of claim 2, wherein said lateral flow device further comprises a control line downstream from said first test line and said second test line, wherein said control line comprises binding moieties that are secondary antibodies that can capture the said indicator, in the presence or absence of βTP.

7. The device of claim 6, wherein said lateral flow device further comprises an absorbent pad disposed downstream from said detection zone and when said control line is present said absorbent pad is disposed downstream from said control line.

8. The device of claim 1, wherein said lateral flow device further comprises a conjugation zone comprising said indicator attached to a βTP binding molecule, where said conjugation zone is disposed in said sample addition zone and/or between said sample addition zone and said detection zone.

9. The device of claim 1, wherein said indicator is selected from the group consisting of a colorimetric indicator, a fluorescent indicator, a radioactive indicator, and a magnetic indicator.

10. The device of claim 1, wherein said βTP binding molecule is an antibody or antibody fragment.

11. The device of claim 1, wherein said binding moieties that bind a complex formed between beta-trace protein (βTP) and an indicator are antibodies or antibody fragments.

12. The device of claim 11, wherein said binding moieties that bind a complex formed between beta-trace protein (βTP) and an indicator are antibodies that specifically bind βTP.

13. The device of claim 1, wherein said device is configured to perform a sandwich assay.

14. The device of claim 1, wherein said porous substrate comprises a material selected from the group consisting of sintered glass or sintered ceramic, a mineral, cellulose, a fiberglass, a nitrocellulose, polyvinylidene fluoride, a nylon, a charge modified nylon, a polyethersulfone, and combinations thereof.

15. A method of determining the presence of a cerebrospinal fluid (CSF) leak in a subject, said method comprising:
applying a nasal drip sample obtained from said subject to the sample application zone of a device of claim 5, wherein said nasal drip sample is diluted 300-fold in a buffer;
operating said device in a lateral-flow assay format and detecting a signal if present at test lines T1 and T2 in a device comprising two test lines and at test lines T1, T2, and T3 in a device comprising three test lines; and
where there is no detectable signal at any test line or a detectable signal at only at test line T1, identifying the subject as a subject having no CSF leak;
where the device comprises two test lines and there is a detectable signal at both test lines T1 and T2 identifying the subject as having a CSF leak;
where the device comprises three test lines and there is a detectable signal at all three test lines T1, T2, and T3, identifying the subject as having a CSF leak; and
where the device comprises three test lines and there is a detectable signal only two test lines T1 and T2, identify the subject as possibly, but not definitely, having a CSF leak and requiring further follow up.

16. The method of claim 15, wherein said method comprises quantifying the nasal drip to serum βTP concentration ratio and a ratio of <2 is classified as negative for the presence of CSF and a ratio of >2 is classified as positive for a CSF leak.

17. A kit for semi-quantification of beta trace protein (βTP) in a biological sample, said kit comprising a container containing a lateral flow device for the semi-quantitative detection of a cerebrospinal fluid leak according to claim 1.

18. The kit of claim 17, wherein said kit contains two barcode-style lateral flow assay (LFA) test devices, one for testing serum and the other for testing a nasal drip sample.

19. The kit of claim 17, wherein said kit further comprises a smartphone-based lateral flow assay (LFA) reader configured to read the test lines on said lateral flow device.

* * * * *